United States Patent [19]

Crouse et al.

[11] Patent Number: 4,884,065
[45] Date of Patent: Nov. 28, 1989

[54] MONITOR FOR DETECTING TUBE POSITION AND AIR BUBBLES IN TUBE

[75] Inventors: Ronald J. Crouse, McKinney; Norris A. Lauer, Mesquite; David A. Pinto, Frisco, all of Tex.

[73] Assignee: Pacesetter Infusion, Ltd., Sylmar, Calif.

[21] Appl. No.: 206,232

[22] Filed: Jun. 13, 1988

[51] Int. Cl.⁴ .............................................. G08B 17/10
[52] U.S. Cl. .................................... 340/632; 250/573; 128/DIG. 13
[58] Field of Search ....................... 340/606, 619, 632; 128/DIG. 12, DIG. 13; 604/250, 258; 250/573, 571; 73/293

[56] References Cited

U.S. PATENT DOCUMENTS

| 3,636,360 | 1/1972 | Oishi et al. ........................ 73/293 X |
| 4,312,341 | 1/1982 | Zissimopoulous et al. ..... 128/DIG. 13 X |
| 4,440,022 | 4/1984 | Mason ............................. 340/619 X |
| 4,658,244 | 4/1987 | Meijer .................... 128/DIG. 13 X |
| 4,788,444 | 11/1988 | Williams ........................... 73/293 X |

Primary Examiner—Joseph A. Orsino
Assistant Examiner—Jeffery A. Hofsass
Attorney, Agent, or Firm—Leslie S. Miller

[57] ABSTRACT

A device for use to detect air in a fluid line between a medication infusion reservoir such as an IV bottle or bag and an IV injection set or a medication infusion pump is disclosed which utilizes a detector apparatus which clamps onto a segment of tubing. The detector uses a light source to generate light which is directed into the tubing, and two light detecting devices, one of which is used to determine whether or not the tubing is properly installed in the detector, and the other of which is used to detect the presence of air in the segment of tubing. The detector works equally well with transparent, translucent, or opaque fluids and includes means for ensuring that the detection system is functioning normally.

19 Claims, 3 Drawing Sheets

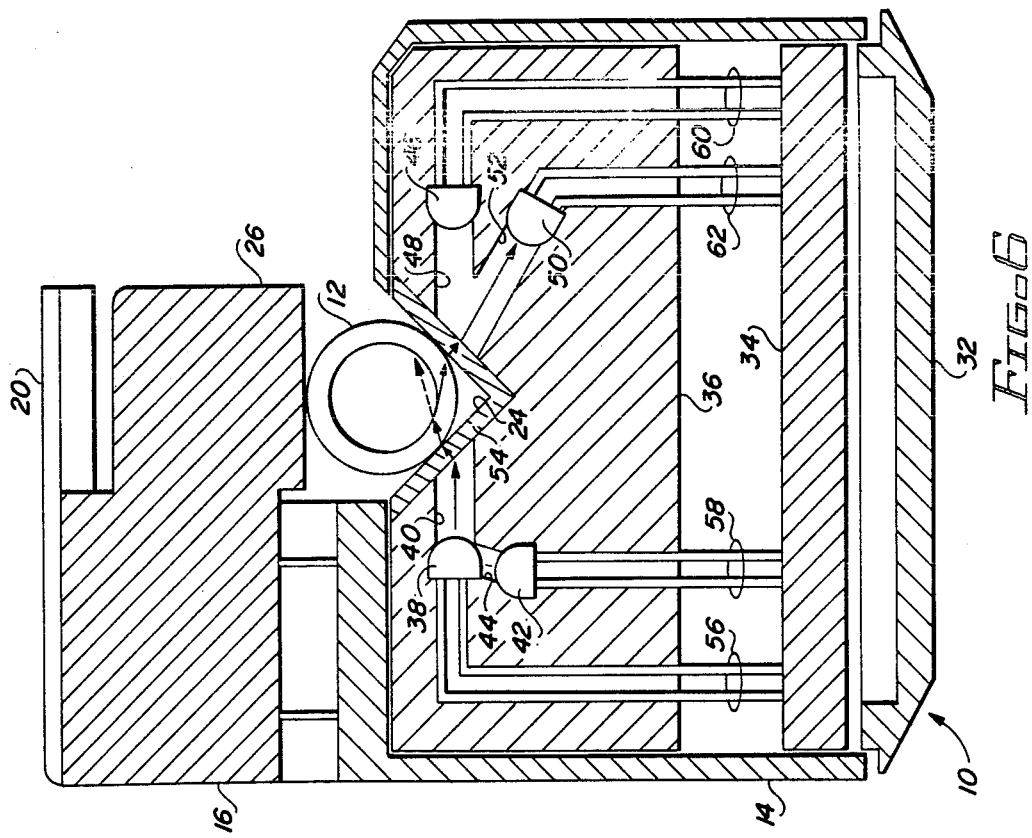
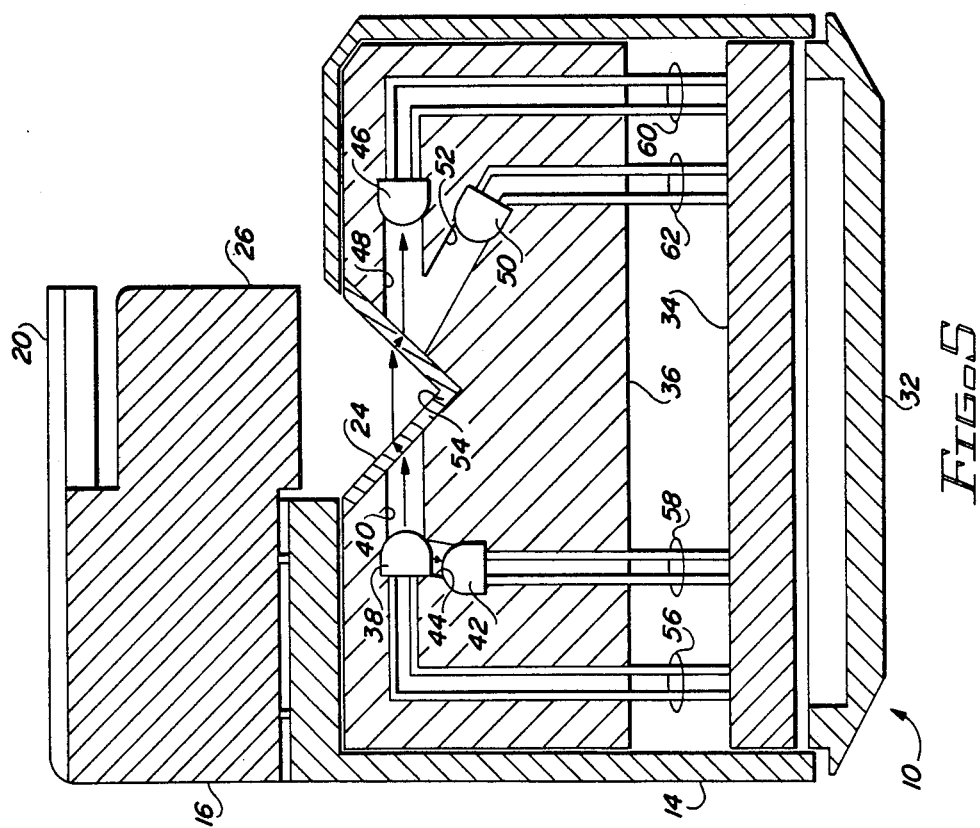

MONITOR FOR DETECTING TUBE POSITION AND AIR BUBBLES IN TUBE

BACKGROUND OF THE INVENTION

Field of the Invention The present invention relates generally to a system for detecting air in a fluid line, and more particularly to a clamp-on detector apparatus for detecting air in the fluid line between a medication infusion reservoir such as an IV bottle or bag and an IV injection set or a medication infusion pump, which detector works equally well with transparent, translucent, or opaque fluids and includes means for ensuring that the detection system is functioning normally.

There are two principal techniques used to administer a continuous flow of medication to a patient, with both techniques involving the administration of a therapeutic fluid from a fluid reservoir or container which is typically an IV bottle. First, medication may be delivered through a conventional IV system using a drip chamber with the injection being made into various IV tubes and the associated paraphernalia, with drop counters being used to meter the amount of fluid delivered. Alternatively, medication infusion pumps may be utilized to administer drugs to a patient in small, precisely metered doses at frequent intervals or, alternatively, in the case of some devices, at a low but essentially continuous rate. Infusion pump therapy is electronically controlled to deliver precise, metered doses at exactly determined intervals.

An essential function of a medication infusion system is to avoid the infusion of fluid containing air bubbles therein. While a small amount of air may be contained in the fluid to be infused in very small air bubbles, larger air bubbles present a real danger to the patient if infused. Although steps may be taken to monitor the fluid line downstream before it reaches the patient to ensure that substantially no air bubbles remain in the fluid which is to be infused, it is also essential to minimize the possibility of air bubbles being contained in fluid near the reservoir end of the infusion apparatus. The detection of air bubbles in all fluids which are to be infused is therefore a critical design requirement.

The introduction of air into the infusion system near the reservoir happens principally when the IV bottle is empty. If the system remains unattended when the fluid reservoir or container is empty, air may be allowed to enter the fluid lines from the reservoir or container end. If no air-in-line detection apparatus is utilized, there is a real danger that IV systems could allow air in the infusion lines. In the case of systems using infusion pumps, even if the pump has an air-in-line detection apparatus, it is generally on the patient side of the pump. This would allow air to reach the infusion pump, and many infusion pumps will not pump air but rather will require repriming.

Many air-in-line detectors known in the art will work with either opaque fluids or with transparent fluids, but require a manual control to be set to the type of fluid being infused. Such detectors rely on the operator to set the control properly, and an operator error could result in the system not working properly and allowing air to pass through the fluid lines without providing an alarm. A detector which will automatically work on either opaque or transparent fluids is disclosed in U.S. Pat. No. 4,114,144, to Hyman. The Hyman detector first detects what type of fluid is in the line, and then provides an alarm if air enters the line.

While the Hyman detector represents an improvement on manual air-in-line detectors, it sacrifices simplicity for its automatic operation, requiring five sets of optical detectors to perform its function. Not only is the Hyman device fairly complex, but it is necessarily relatively larger and more expensive to manufacture than desirable. As may be see from the Hyman reference, the device is a built-in detector rather than an accessory detector, and is used (in the preferred embodiment) downstream of a pump. Due to its size, it is not readily useable as a standalone device, or as an empty container detector.

It is therefore the primary objective of the present invention to provide an empty container detection system for use either a conventional IV system or in conjunction with an infusion pump unit. The system of the present invention must be simple and easy to use, and must clamp onto a fluid line immediately downstream from the fluid reservoir or container. The empty container detection system of the present invention must be capable of immediately, accurately, and effectively detecting air in the fluid line regardless of whether the fluid being infused is opaque or transparent. The system must be fully automatic, not requiring any setup or intervention by an operator except clipping the device onto a line and plugging it in to the main pump unit or other controller.

Several other additional features are desirable in the design of the empty container detection system. One such feature is the ability to detect air bubbles whether the flow rate of the fluid in the line is fast or slow. In addition to being able to detect air in the fluid line, the system must also be accurate, presenting a high degree of resistance to false alarms. Since the detector of the system is to clip onto the fluid line, it must be small and light in size.

Despite the inclusion of all of the aforesaid features, the system of the present invention shall utilize a minimum number of parts, all of which parts are of inexpensive construction, yet which afford the empty container detector system of the present invention the high degree of accuracy which must be retained. The system of the present invention must also be of a design which enables it to compete economically with known competing systems, and it must provide an ease of use rivaling the best of competing systems. The system must accomplish all these objects in a manner which will retain and enhance all of the advantages of reliability, durability, and safety of operation. The system of the present invention must provide all of these advantages and overcome the limitations of the background art without incurring any relative disadvantage. All the advantages of the present invention will result in a empty container detector having a number of advantages making it a highly desirable alternative to systems presently available.

SUMMARY OF THE INVENTION

The disadvantages and limitations of the background art discussed above are overcome by the present invention. With this invention, a clamp-on empty container device is used to detect the presence of air bubbles in a segment of tubing around which segment the device is clamped. The device uses a light-emitting diode (LED) which is periodically triggered to produce a burst of light at a desired sampling rate determined by the frequency of the triggering signal. If the tubing is empty of fluid or an air bubble is passing therethrough, the light is reflected at the inner diameter of the tubing and directed onto a liquid in tube sensor. If the liquid in tube sensor detects light, the signal is indicative of air in the tubing, and an alarm will be given.

If there is transparent fluid within the tubing, the light will pass through the tubing without being reflected toward the liquid in tube sensor, in which case the light will not be directed onto the liquid in tube sensor. Rather, the light will continue in a path through the transparent fluid, and through the opposite side of the tubing. Since the liquid in tube sensor is not located in line on the opposite side of the tubing, it will not detect the light. This is an indication that there is fluid in the tube.

Similarly, if there is opaque fluid within the tubing, the light will pass through the tubing without being reflected, and again the light will not be directed onto the liquid in tube sensor. The light will continue in a path into the opaque fluid, and will be absorbed by the opaque fluid. Since the liquid in tube sensor does not detect the light, an indication is made that there is fluid in the tubing.

The device of the present invention is therefore able to discriminate between air and fluid, regardless of whether the 10 fluid is transparent or opaque. In addition, the inherent design of the present invention requires only a single light source and light sensor. In the preferred embodiment of the present invention, an additional sensor is used to compensate for LED performance degradation caused by temperature and aging of the LED. This sensor may also be used to verify that the light source (the LED) is in fact operating properly and is emitting light. Another additional sensor is used to verify that the tubing is properly situated in the device. By using these additional sensors, the proper operation of the system is ensured.

The packaging of the system of the present invention is designed to be as size-efficient and easy-to-use as possible. The system is packaged in a clamp which may be clipped on to the supply tubing near the fluid reservoir. The system of the preferred embodiment is geometrically designed to work on either of two sizes of tubing, both of which are commonly used in medication infusion applications. The detector may easily be clamped onto the tubing using only one hand, and is lightweight to allow the device to be supported by the tubing, thereby not requiring additional support apparatus.

The device in the preferred embodiment is designed to be used with a medication infusion pump, and may be plugged into the main pump unit. Accordingly, the empty container detector of the present invention may be driven by the main pump unit, and need not itself contain a power supply or the apparatus to generate the audible or visible alarm from a signal indicating air in the tubing. Such apparatus, of course, could be added to make the detector a stand-alone device. In the preferred embodiment circuitry is included to minimize the power requirements of the detector by operating the system periodically rather than on a continuous basis. Finally, the system may also contain circuitry for compensating for LED degradation or varying ambient light conditions.

The present invention thus provides an empty container detection system which may be used with a conventional IV system, or (as in the preferred embodiment) in conjunction with an infusion pump unit. The system of the present invention must be simple and easy to use, and must clamp onto a fluid line immediately downstream from the fluid reservoir or container. The empty container detection system of the present invention must be capable of immediately, accurately, and effectively detecting air in the fluid line regardless of whether the fluid being infused is opaque, translucent, or transparent. The system must be fully automatic, not requiring any setup or intervention by an operator except clipping the device onto a line and plugging it in to the main pump unit or other controller.

Several other additional features are desirable in the design of the empty container detection system. One such feature is the ability to detect air bubbles whether the flow rate of the fluid in the line is fast or slow. In addition to being able to detect air in the fluid line, the system must also be accurate, presenting a high degree of resistance to false alarms. Since the detector of the system is to clip onto the fluid line, it must be small and light in size.

Despite the inclusion of all of the aforesaid features, the system of the present invention shall utilize a minimum number of parts, all of which parts are of inexpensive construction, yet which afford the empty container detector system of the present invention the high degree of accuracy which must be retained. The system of the present invention must also be of a design which enables it to compete economically with known competing systems, and it must provide an ease of use rivaling the best of competing systems. The system must accomplish all these objects in a manner which will retain and enhance all of the advantages of reliability, durability, and safety of operation. The system of the present invention must provide all of these advantages and overcome the limitations of the background art without incurring any relative disadvantage. All the advantages of the present invention will result in a empty container detector having a number of advantages making it a highly desirable alternative to systems presently available.

DESCRIPTION OF THE DRAWINGS

These and other advantages of the present invention are best understood with reference to the drawings, in which:

FIG. 5 is a sectional view of the empty container detector shown in FIGS. 1 through 4, without the device being attached to tubing;

FIG. 6 is a sectional view of the empty container detector shown in FIGS. 1 through 5 with a segment of tubing in the fluid line of a medication infusion system being mounted in the device;

DETAILED DESCRIPTION OF THE PREFERRED EMBODIMENT

Figure 1:
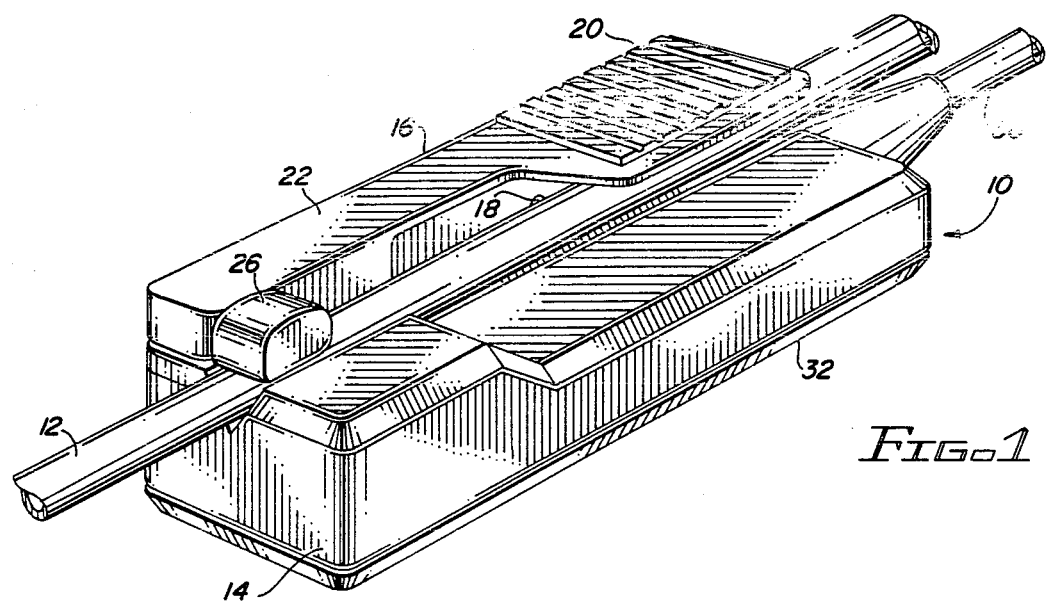
FIG. 1 is a perspective view of the empty container detector of the present invention clamped onto a segment of tubing in the fluid line of a medication infusion system.
Figure 2:
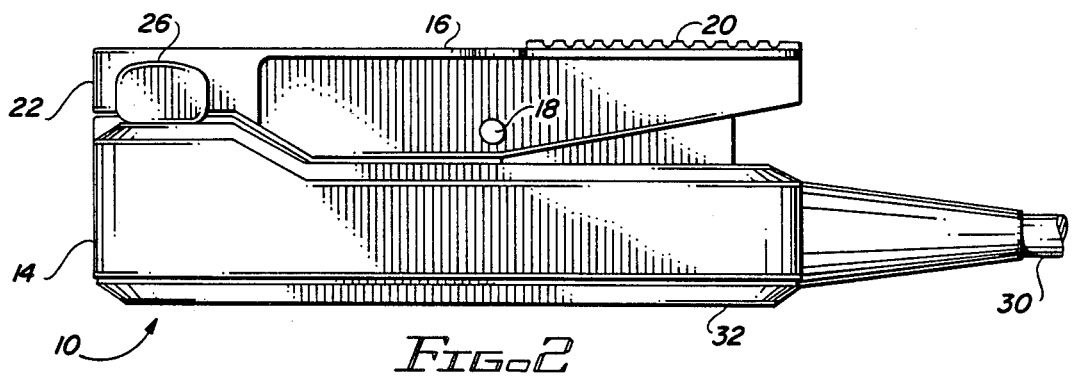
FIG. 2 is a side view of the empty container detector shown in FIG. 1 with the tubing removed.

The preferred embodiment of the present invention is illustrated in FIG. 1, in which an empty container detector 10 is shown clamped on to a segment of tubing 12. The empty container detector 10 includes a base portion 14, and a clamping arm 16 pivotally mounted onto the base portion 14. The point of rotation of the clamping arm 16 is at the center thereof, and a pin 18 is used to pivotally mount the clamping arm 16 on the base portion 14, as best shown in FIG. 2. The clamping arm 16 has a grip portion 20 at one end thereof, and a clamping portion 22 at the other end thereof.

Figure 3:
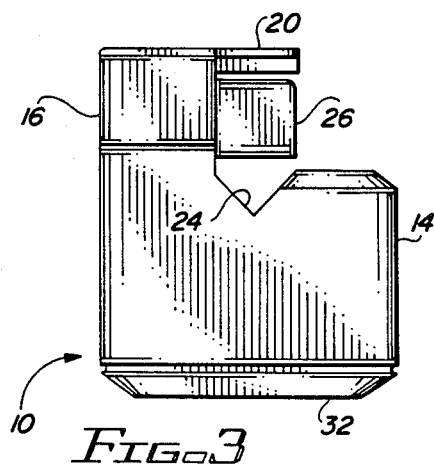
FIG. 3 is an end view of the empty container detector shown in FIGS. 1 and 2.

Referring next to FIG. 3, which shows the end of the empty container detector 10 used to grip the segment of tubing 12 (FIG. 1), there is a V-shaped recess 24 in the base portion 14 at that end of the empty container detector 10. This V-shaped recess 24 is the portion of the empty container detector 10 into which the segment of tubing 12 (FIG. 1) is placed. The clamping portion 22 of the clamping arm 16 includes a clamping segment 26 which is located directly over the V-shaped recess 24 in the base portion 14, which clamping segment 26 is used to retain the segment of tubing 12 (FIG. 1) in the V-shaped recess 24.

Figure 4:
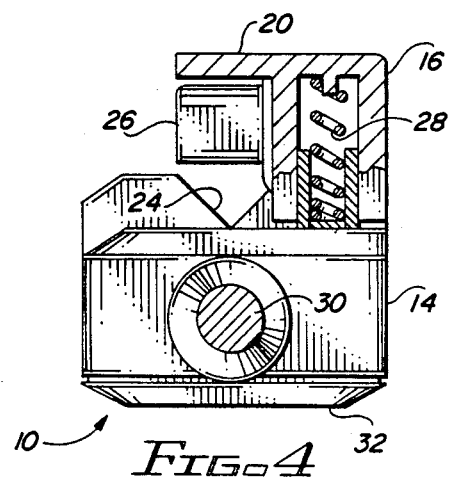
FIG. 4 is another end view of the empty container detector shown in FIGS. 1 through 3, partially cut away to illustrate the spring used to bias the clamp arm of the detector onto the tubing to retain the detector in position on the tubing.

The clamping arm 16 is spring biased to urge the clamping segment 26 of the clamping arm 16 toward the V-shaped recess 24 in the base portion 14. Referring to FIG. 4, a spring 28 is located between the grip portion 20 of the clamping arm 16 and the base portion 14, and urges the grip portion 20 of the clamping arm 16 upward away from the base portion 14. This bias causes the clamping arm 16 to rotate, with the clamping portion 22 of the clamping arm 16 and the clamping segment 26 thereon being urged downward toward the V-shaped recess 24.

Referring generally to FIGS. 1 through 4, it will be appreciated that to clamp the empty container detector 10 onto the segment of tubing 12, the grip portion 20 of the clamping arm 16 is squeezed toward the base portion 14, forcing the clamping segment 26 away from the V-shaped recess 24. The segment of tubing 12 is placed with a portion of the segment of tubing 12 in the V-shaped recess 24, and the grip portion 20 of the clamping arm 16 is released, allowing the spring 28 to force the clamping segment 26 down onto the top of the portion of the segment of tubing 12 located in the V-shaped recess 24. The force with which the clamping segment 26 is urged onto the segment of tubing 12 is great enough to retain it in position as shown in FIG. 1, although if a cord 30 containing wires (not shown) to carry electrical signals to and from the empty container detector 10 is pulled sharply, the empty container detector 10 will slide on the segment of tubing 12.

In the preferred embodiment, since the empty container detector 10 is used to detect when fluid from a reservoir (not shown) is exhausted, the segment of tubing 12 that the empty container detector 10 would be mounted onto would be located as close as feasible to the reservoir (not shown). Since the empty container detector 10 of the present invention could be used at any location as a bubble detector, it will be realized by those skilled in the art that the empty container detector 10 could be located on tubing at various locations in the wide variety of different infusion setups possible.

Referring next to FIG. 5, some of the electronic components located inside the base portion 14 are illustrated. The bottom of the base portion 14 is closed with a back 32 to seal and protect the electronic components located therein. Located near the bottom of the inner portion of the base portion 14 is a circuit board 34, which contains a number of electrical components (not shown but discussed below) thereon. Located in the base portion 14 near the top thereof is an LED mounting block 36 having an LED 38 which is a light source and three sensors mounted therein.

The LED 38 is located on one side of the V-shaped recess 24, and will shine light through a channel 40 in the LED mounting block 36 across the V-shaped recess 24. Located on the side of the LED 38 is an LED sensor 42, with a channel 44 in the LED mounting block 36 allowing light from the LED 38 to reach the LED sensor 42. Located directly across the V-shaped recess 24 from the LED 38 is a tube/no tube sensor 46, with a channel 48 in the LED mounting block 36 allowing light shining directly across the V-shaped recess 24 from the LED 38 to reach the tube/no tube sensor 46. Located below the tube/no tube sensor 46 is a liquid in tube sensor 50, with a channel 52 leading downward from the V-shaped recess 24 to the liquid in tube sensor 50.

Located at the V-shaped recess 24 and mounted onto the LED mounting block 36 is a V-shaped filter 54, which acts to filter out extraneous light frequencies. In the preferred embodiment, the V-shaped filter 54 is a polysulfone filter, which allows only infrared (IR) light to pass therethrough, the LED 38 generates IR light, and the LED sensor 42, the tube/no tube sensor 46, and the liquid in tube sensor 50 all sense IR light. The LED mounting block 36 is supported above the circuit board 34 by a pair of leads 56 extending from the LED 38 to the circuit board 34, a pair of leads 58 extending from the LED sensor 42 to the circuit board 34, a pair of leads 60 extending from the tube/no tube sensor 46 to the circuit board 34, and a pair of leads 62 extending from the liquid in tube sensor 50 to the circuit board.

The basic operation of the empty container detector 10 of the present invention may be described with reference to FIG. 6. The segment of tubing 12 is located in the V-shaped recess 24. The LED 38 generates light, which is detected by the LED sensor 42, which is used to compensate for fluctuations in the light level from the LED 38 caused by temperature variations and other factors including degradation in performance of the LED 38 due to aging. In the preferred embodiment this is accomplished by using the LED sensor 42 to detect a particular light level which is less than the maximum light level, and take a reading at that time of the output of the liquid in tube sensor 50. By doing so, it is ensured that the measurement of light taken by the liquid in tube sensor 50 will always be taken at a constant light level, which in the preferred embodiment occurs at the point of the light impulse from the LED 38 is falling off. In the preferred embodiment, the LED sensor 42 may also be used to confirm that the LED 38 is indeed generating light. If the LED 38 were to suddenly suffer catastrophic failure, an alarm could then be provided.

If the segment of tubing 12 is properly located in the V-shaped recess 24, the light from the LED 38 will be refracted by the segment of tubing 12, and will not reach the tube/no tube sensor 46. If the segment of tubing 12 is not located in the V-shaped recess 24, light will reach the tube/no tube sensor 46, indicating that the segment of tubing 12 is not properly located in the V-shaped recess 24. It should be noted that whether or not fluid is contained in the segment of tubing 12 is not relevant to whether or not the light from the LED 38 reaches the tube/no tube sensor 46. As will become apparent below, either way if the segment of tubing 12 is properly located in the V-shaped recess 24, light from the LED 38 will not reach the tube/no tube sensor 46, thereby indicating that the segment of tubing 12 is properly located in the V-shaped recess 24.

When the segment of tubing 12 is properly located in the V-shaped recess 24, light from the LED 38 will be refracted by the outer wall of the segment of tubing 12 in an upward direction through the wall of the segment of tubing 12 as shown in FIG. 6. If this light encounters air (which term "air" is used generically to indicate an air bubble or greater quantities of air) in the segment of tubing 12, the light will be reflected off the inner wall of the segment of tubing 12 in a downward direction, with the light then being directed onto the liquid in tube sensor 50. It should be noted that small amounts of light will be refracted by the segment of tubing 12, and reflected off the opposite side of the inner diameter of the segment of tubing 12, but these amounts are not significant in the sense that they are insufficient to operate the liquid in tube sensor 50. The angle at which light is reflected off of the inner wall of the segment of tubing 12 is a critical angle, since it must be selected to direct the light such that it will reach the liquid in tube sensor 50. Accordingly, if the liquid in tube sensor 50 detects light it is an indication that air is contained in the segment of tubing 12.

If transparent fluid is contained in the segment of tubing 12, light from the LED 38 which is refracted by the outer wall of the segment of tubing 12 in an upward direction through the wall of the segment of tubing 12 will continue in that direction as indicated by the dotted line. In this case, the light will not reach the liquid in tube sensor 50, indicating that there is fluid in the segment of tubing 12. If opaque fluid is contained in the segment of tubing 12, light from the LED 38 which is refracted by the outer wall of the segment of tubing 12 in a upward direction through the wall of the segment of tubing 12 will be directed into the opaque fluid, and will be substantially absorbed by the opaque fluid. Again in this case, the light will not reach the liquid in tube sensor 50, indicating that there is fluid in the segment of tubing 12. In the case of translucent fluid, of course, part of the light will be absorbed by the fluid and part will pass through the fluid, but substantially no light will reach the liquid in tube sensor 50.

Figure 7:
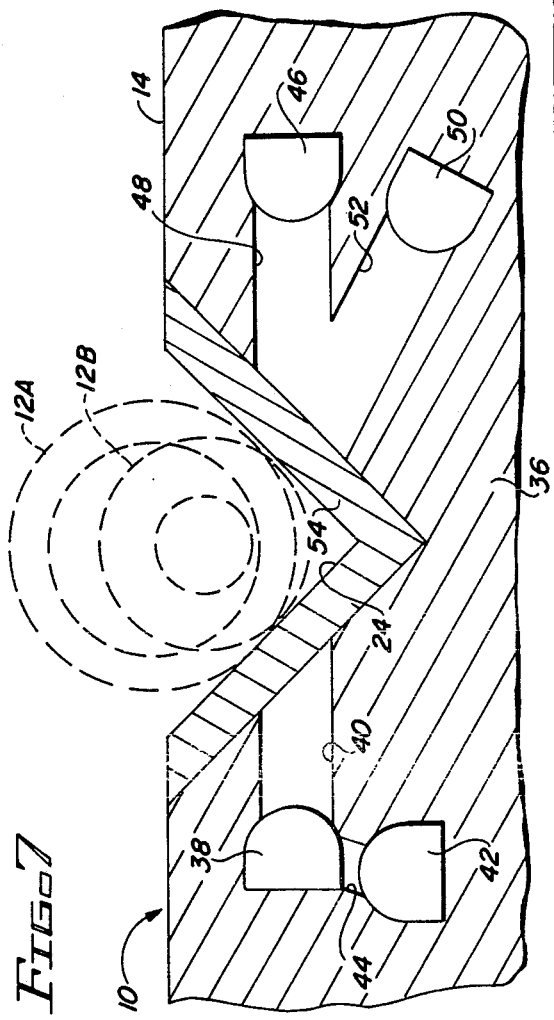
FIG. 7 is a partial sectional view of the base portion of the empty container detector shown in FIGS. 1 through 6, illustrating the geometric design of the device which allows it to work with two different sizes of tubing.

It will now be apparent to those skilled in the art that the direction of reflection (and refraction) of the light in tubing containing air is dependent on the geometry of the device. In other words, the geometry of the device is designed to direct light onto the liquid in tube sensor 50 when air is contained in the segment of tubing 12. Referring now to FIG. 7, two sizes 15 of tubing are illustrated in dotted lines—a larger tubing 12A and a smaller tubing 12B, with the two sizes 12A and 12B representing the two sizes of tubing used most frequently in the field of medication infusion. By designing the configuration and size of the V-shaped recess 24, the thickness of the V-shaped filter 54, and the relative locations of the LED 38 and the liquid in tube sensor 50, the empty container detector 10 will work identically for the two different sized of tubing 12A and 12B. It may also be noted that the clamping action of the clamping segment 36 (FIGS. 1 through 6) may act to distort somewhat the shape of the segment of tubing 12, and this factor may enter into the geometric design of the device.

It is apparent from FIG. 7 that the outer diameters of the tubing 12A and the tubing 12B coincide at the points at which light would enter the tubing from the V-shaped filter 54 and at the point at which light would leave tubing containing air and enter the V-shaped filter 54 on its way to the liquid in tube sensor 50. Similarly, the inner diameters of the tubing 12A and the tubing 12B are relatively located so as to reflect light off the inner walls thereof at the same critical angle to direct the light onto the liquid in tube sensor 50.

Figure 8:
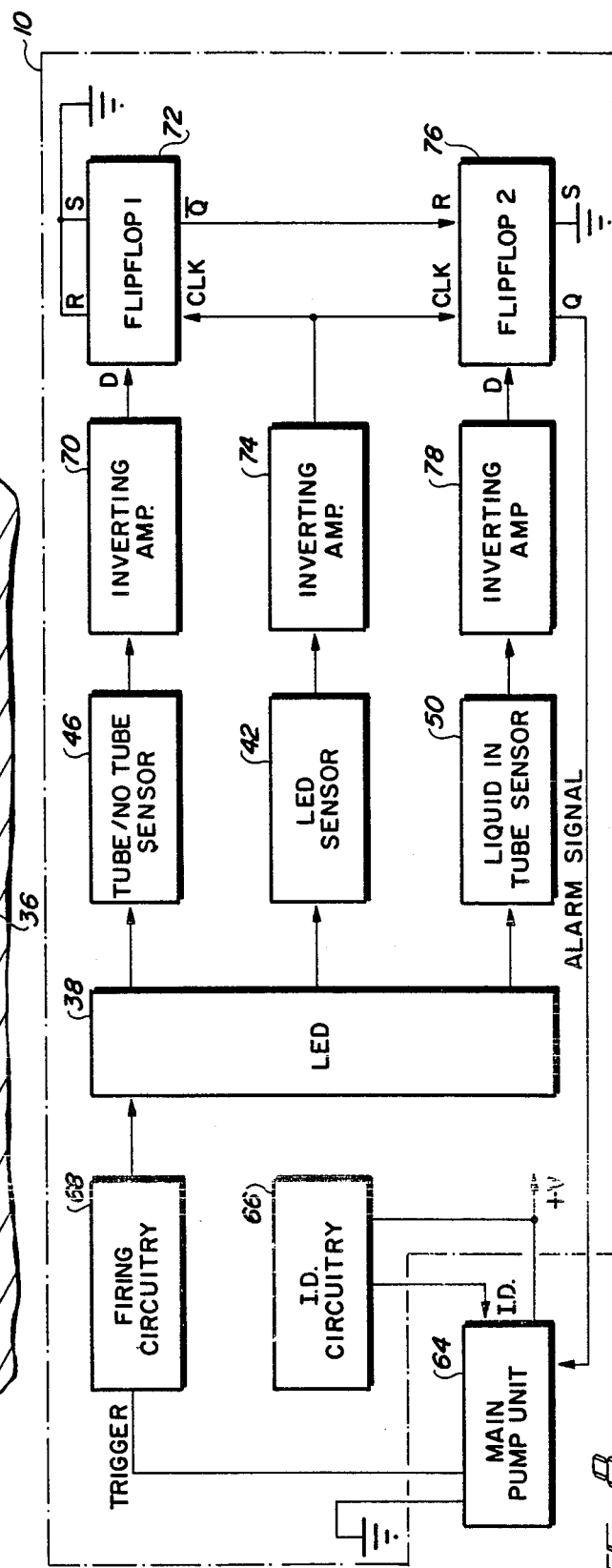
FIG. 8 is a block diagram of the operation of the system 10 of the present invention.

Referring now to FIG. 8, a block diagram of a circuit which could be used by the empty container detector 10 of the present invention is illustrated. It will be appreciated that the electronic components of the empty container detector 10 not specifically described above are all mounted on the circuit board 34 (FIGS. 5 and 6). A main pump unit 64 is used in conjunction with the empty container detector 10 of the present invention. (It will be appreciated by those skilled in the art that the electronic components could also be mounted in the main pump unit 64 instead of inside the empty container detector 10 on the circuit board 34.) The main pump unit 64 supplies power to the empty container detector 10 via a +V wire and a ground connection. It should be noted that the various components of FIG. 8 are connected to +V and ground, although these connections are not expressly shown in FIG. 8.

Other connections between the main pump unit 64 and the empty container detector 10 include a trigger signal, an I.D. signal, and an alarm signal. These five connections between the main pump unit 64 and the empty container detector 10 would be contained in the cord 30 (FIGS. 1 and 2) extending from the empty container detector 10. The I.D. signal is optional, and in the preferred embodiment I.D. circuitry 66 is used to indicate to the main pump unit 64 either that the cord 30 (FIGS. 1 and 2) from the empty container detector 10 is properly connected to the main pump unit 64, or the type of device which is plugged in to the main pump unit 64.

In the former case, the I.D. circuitry 66 need only feed the +V signal back to the main pump unit 64 as the I.D. signal to indicate that the empty container detector 10 is properly connected to the main pump unit 64. As such, if the main pump unit 64 does not detect +V on the I.D. signal line, it will be an indication that the empty container detector 10 is not properly connected to the main pump unit 64. In the latter case, the I.D. circuitry 66 includes a resistor (not shown), with the size of the resistor indicating to the main pump unit 64 (by the returning current) which particular device is plugged into the main pump unit 64. For example, three different resistances could be used in three different devices which may be plugged into the main pump unit 64, with one of these three different devices being the empty container detector 10 of the present invention.

Firing circuitry 68 is included in the empty container detector 10 to conserve power. Rather than having the LED 38 on all the time, it may be strobed periodically by the firing circuitry 68 in response to the trigger signal from the main pump unit 64. The rate at which the LED 38 is strobed depends on several factors, including tubing size and maximum flow rate. In the preferred embodiment, the rate is sufficiently fast to prevent an air bubble from moving through the segment of tubing 12 without being detected.

The tube/no tube sensor 46 supplies an output to an inverting amplifier 70, which in turn provides an output which is the Data (D) input to a first D flip-flop 72. The Direct Reset (R) and Direct Set (S) inputs of the first D flip-flop 72 are both inactive (tied to ground). The LED sensor 42 supplies an output to a inverting amplifier 74, which in turn provides an output which is the Clock signal for both the first D flip-flop 72 and a second D flip-flop 76. In the preferred embodiment the Clock signal occurs when the signal from the LED sensor 42 has decayed to a predetermined light level which is less than the maximum light level. This is accomplished by using the inverting amplifier 74 to provide the Clock signal when the decaying signal from the LED sensor 38 has dropped to the predetermined level, causing the system to take a reading of the liquid in tube sensor 50 at that time. This operation ensures that the measurement of light taken by the liquid in tube sensor 50 will always be taken at a constant light level, which in the preferred embodiment is the point at which the light impulse from the LED 38 has fallen off to the predetermined level. The $\overline{Q}$ output from the first D flip-flop 72 is supplied to the second D flip-flop 76 as the R input. The liquid in tube sensor 50 supplies an output to an inverting amplifier 78, which in turn provides an output which is the D input to the second D flip-flop 76. The S input to the second D flip-flop 76 is inactive (grounded). Finally, the Q output of the second D flip-flop 76 is supplied to the main pump unit 64 as the alarm signal.

Although those skilled in the art will readily understand 15 the operation of the system as above described, it may be helpful to add a brief description of the operation of the circuit of FIG. 8. First, with regard to the output of the inverting amplifier 74, which is the Clock input to the first D flip-flop 72 and the second D flip-flop 76, when the LED 38 is pulsed and the light is detected by the LED sensor 42, the output of the inverting amplifier 74 will go low. When the light from the LED 38 diminishes, the output of the inverting amplifier 74 will go high, causing the first D flip-flop 72 and the second D flip-flop 76 to cycle. The Clock pulse from the inverting amplifier 74 will go high when the light level from the LED 38 has dropped to the preselected level. By operating the Clock in this manner, the circuit will be operational with the light level at a uniform, preselected level, thereby eliminating problems due to ambient light, thermal and age degradation of the LED 38, and supply voltage variations.

If the output from the tube/no tube sensor 46 is high (indicating that the segment of tubing 12 is not properly installed), the output from the inverting amplifier 70 and the D input to the first D flip-flop 72 will be low. If the D input to the first D flip-flop 72 is low, then the $\overline{Q}$ output from the first D flip-flop 72 will be high. The $\overline{Q}$ output from the first D flip-flop 72 is the R input to the second D flip-flop 76, and if the R input to the second D flip-flop 76 is active (high), the Q output of the second D flip-flop 76 is always inactive (low). For the preferred embodiment of the present invention, a low Q output from the second D flip-flop 76 will cause an alarm. It is therefore apparent that if the output of the tube/no tube sensor 46 is high, an alarm will be sounded regardless of the state of the liquid in tube sensor 50.

The reason for having a low Q output from the second D flip-flop 76 cause an alarm instead of a high level causing an alarm is that if the connection between the empty container detector 10 and the main pump unit 64 were broken, the alarm signal input to the main pump unit 64 would be low. It is therefore a sound design to use a low output from the second D flip-flop 76 as an alarm state.

If the output of the tube/no tube sensor 46 is low (indicating the segment of tubing 12 is properly installed), the output $\overline{Q}$ of the first D flip-flop 72 will be inactive (low). In this case, the state of the liquid in tube sensor 50 will determine whether or not an alarm is sounded. If the output of the liquid in tube sensor 50 is high (indicating that air is in the segment of tubing 12), the output of the inverting amplifier 78 will then be low. THe output of the inverting amplifier 78 is the D input to the second D flip-flop 76, and if the D input to the second D flip-flop 76 is low, the Q output of the second D flip-flop 76 will be low, causing an alarm.

If, with the output of the tube/no tube sensor 46 still low (indicating the segment of tubing 12 is properly installed), the output of the liquid in tube sensor 50 is high (indicating that no air is contained in the segment of tubing 12), the output of the inverting amplifier 78 is high. Accordingly, the D input to the second D flip-flop 76 is high, and the Q output of the second D flip-flop 76 will be high, and no alarm will be sounded.

Of course, it will be appreciated by those skilled in the art that the circuit of FIG. 8 represents but one of a number of different circuits which could be used to achieve the same result. The important thing is that: 1. whenever the output of the tube/no tube sensor 46 is high, an alarm be sounded (indicating that the segment of tubing 12 is not properly installed; and 2. when the output of the tube/no tube sensor 46 is low, an alarm is sounded when the output of the liquid in tube sensor 50 is high.

It will be appreciated that a visual alarm mechanism and/or an audible alarm mechanism is contained in the main pump unit 64. For example, the visible alarm mechanism could be a flashing light or a word on a screen indicating an alarm, and the audible alarm mechanism could be a buzzer, horn, or electronically generated tone. It will be apparent to those skilled in the art that these mechanisms could alternatively contained in the empty container detector 10 itself. Likewise, the power supply and oscillator means to generate the trigger signal could also be contained in the empty container detector 10 itself. THese modifications are considered to be within the spirit of the present invention, although they are not the preferred embodiment.

It may thus be perceived that the present invention provides an empty container detection system which is simple and easy to use, clamping onto a fluid line immediately downstream from the fluid reservoir or container. The empty container detection system of the present invention is capable of quickly, accurately, and effectively detecting air in the fluid line regardless of whether the fluid being infused is opaque, translucent, or transparent. The system is fully automatic, and does not require any setup or intervention by an operator except clipping the device onto a line and plugging it in to the main pump unit.

Other desirable features in the design of the empty container detection system of the present invention include the small size and light weight of the clamp on sensor and the ability to detect air bubbles whether the flow rate of the fluid in the line is fast or slow. In addition to being able to detect air in the fluid line, the system is highly accurate, and presents a high degree of resistance to false alarms. Despite the inclusion of all of the aforesaid features, the system of the present invention utilizes a minimum number of parts in a compact construction, is of inexpensive construction, and yet features a high degree of accuracy. The system of the present invention is thus able to compete economically with known competing systems, and provides an ease of use rivaling the best of such competing systems. The system accomplishes all these objects in a manner which retains and enhances all of the advantages of reliability, durability, and safety of operation, and does so without incurring any relative disadvantage. All the advantages of the present invention result in a empty container detector having a number of advantages making it a highly desirable alternative to systems presently available.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A device for detecting the presence of air in hollow cylindrical tubing, comprising:
   means for mounting a plurality of components therein, said mounting means including a recessed groove therein, said recessed groove for receiving a portion of the tubing;
   a light source located in said mounting means on one side of said recessed groove, light from said light source being directed onto said tubing when the tubing is located in said recessed groove;
   a tube/no tube light sensor located in said mounting means on the other side of said recessed groove from said light source, said tube/no tube light sensor receiving light from said light source whenever tubing is not located in said recessed groove, said tube/no tube light sensor receiving substantially no light from said light source whenever tubing is located in said recessed groove; and
   a liquid in tube light sensor located in said mounting means, light from said light source which enters tubing located in said recessed groove being reflected off the inside of the tubing and directed onto said liquid in tube light sensor whenever air is contained in the tubing, substantially no light entering tubing located in said recessed groove being reflected off the inside of the tubing and being directed onto said liquid in tube light sensor whenever fluid is contained in the tubing, light entering tubing located in said recessed groove instead entering the fluid contained in the tubing.

2. A device as defined in claim 1, additionally comprising:
   an operating characteristic light sensor for monitoring the light produced by said light source, said operating characteristic light sensor producing an output signal indicative of the light produced by said light source.

3. A device as defined in claim 2, wherein said operating characteristic light sensor monitors said light sensor to ensure that said light sensor is operating properly, additionally comprising:
   means for providing an alarm if said light sensor is substantially inoperative.

4. A device as defined in claim 2, additionally comprising:
   means for monitoring said output signal from said operating characteristic light sensor, said monitoring means causing said tube/no tube sensor and said liquid in tube sensor to measure the relative amounts of light detected by said tube/no tube sensor and said liquid in tube sensor when the level of light output from said light source is at a preselected level.

5. A device as defined in claim 4, wherein said preselected level is a level below the maximum level of light generated by said light source, and occurs when the level of light generated by said light source has fallen from a higher level to said preselected level.

6. A device as defined in claim 1, wherein said recessed groove is essentially V-shaped.

7. A device as defined in claim 6, wherein said light source generates infrared light and said tube/no tube light sensor and said liquid in tube light sensor sense infrared light, additionally comprising:
   a V-shaped filter adjacent said recessed groove, said V-shaped filter allowing only infrared (IR) light to pass therethrough.

8. A device as defined in claim 7 wherein said V-shaped filter is a polysulfone filter.

9. A device as defined in claim 7, wherein said V-shaped filter is so geometrically arranged and configured as to make said device work identically for two different predetermined sizes of tubing 10. A device as defined in claim 9, wherein the outer diameters of the two different predetermined sizes of tubing coincide at the points at which light would enter the tubing from said V-shaped filter and at the point at which light would leave tubing containing air and enter the V-shaped filter in a path to said liquid in tube light sensor, and the inner diameters of the two different predetermined sizes of tubing are relatively located so as to reflect light off the inner walls thereof at the same critical angle to direct the light onto said liquid in tube light sensor.

11. A device as defined in claim 1, additionally comprising:
   means for retaining tubing in said recessed groove.

12. A device as defined in claim 11, wherein said retaining means comprises:
   a clamping arm pivotally mounted on said mounting means, said clamping arm including a clamping segment located over said recessed groove; and
   means for biasing said clamping segment of said clamping arm toward said recessed groove.

13. A device as defined in claim 12, wherein said clamping arm also includes a grip portion at the end of said clamping arm opposite said clamping segment for opening said clamping arm to allow tubing to be installed into or removed from said recessed groove.

14. A device as defined in claim 12, wherein said biasing means comprises a spring.

15. A device as defined in claim 1, additionally comprising:
   first alarm means for generating an alarm signal whenever said tube/no tube light sensor receives substantial light from said light source to indicate that tubing is not located in said recessed area; and second alarm means for generating an alarm signal whenever said liquid in tube sensor receives substantial light from the inside of the tubing.

16. A device as defined in claim 1, additionally comprising:
means for identifying said device to a main pump unit which said device is connected to.

17. A device as defined in claim 16, wherein said identifying means comprises:
a first preselected resistance which may be sensed by the main pump unit to identify said device.

18. A device for detecting the presence of air in hollow cylindrical tubing, comprising:
means for mounting a plurality of components therein, said mounting means including a recessed groove therein, said recessed groove for receiving a portion of the tubing;
a clamping arm pivotally mounted on said mounting means, said clamping arm including a clamping segment located over said recessed groove;
means for biasing said clamping segment of said clamping arm toward said recessed groove;
a light source located in said mounting means on one side of said recessed groove, light from said light source being directed onto said tubing when the tubing is located in said recessed groove;
a tube/no tube light sensor located in said mounting means on the other side of said recessed groove from said light source, said tube/no tube light sensor receiving light from said light source whenever tubing is not located in said recessed groove, said tube/no tube light sensor receiving substantially no light from said light source whenever tubing is located in said recessed groove;
first alarm means for generating an alarm signal whenever said tube/no tube light sensor receives substantial light from said light source to indicate that tubing is not located in said recessed area;
a liquid in tube light sensor located in said mounting means, light from said light source which enters tubing located in said recessed groove being reflected off the inside of the tubing and directed onto said liquid in tube light sensor whenever air is contained in the tubing, substantially no light entering tubing located in said recessed groove being reflected off the inside of the tubing and being directed onto said liquid in tube light sensor whenever fluid is contained in the tubing, light entering tubing located in said recessed groove instead entering the fluid contained in the tubing; and
second alarm means for generating an alarm signal whenever said liquid in tube sensor receives substantial light from the inside of the tubing.

19. A method for detecting the presence of air in hollow cylindrical tubing, comprising:
providing means for mounting a plurality of components therein, said mounting means including a recessed groove therein, said recessed groove for receiving a portion of the tubing;
directing light from a light source located in said mounting means on one side of said recessed groove onto said tubing when the tubing is located in said recessed groove;
detecting whether or not tubing is properly located in said recessed groove with a tube/no tube light sensor located in said mounting means on the other side of said recessed groove from said light source, said tube/no tube light sensor receiving light from said light source whenever tubing is not located in said recessed groove, said tube/no tube light sensor receiving substantially no light from said light source whenever tubing is located in said recessed groove; and
detecting whether or not air is contained in the tubing with a liquid in tube light sensor located in said mounting means, light from said light source which enters tubing located in said recessed groove being reflected off the inside of the tubing and directed onto said liquid in tube light sensor whenever air is contained in the tubing, substantially no light entering tubing located in said recessed groove being reflected off the inside of the tubing and being directed onto said liquid in tube light sensor whenever fluid is contained in the tubing, light entering tubing located in said recessed groove instead entering the fluid contained in the tubing.

* * * * *

UNITED STATES PATENT AND TRADEMARK OFFICE
CERTIFICATE OF CORRECTION

PATENT NO. : 4,884,065
DATED : November 28, 1989
INVENTOR(S) : Ronald J. Crouse; Norris A. Lauer; David A. Pinto It is certified that error appears in the above-indentified patent and that said Letters Patent is hereby corrected as shown below:

```
In Column 2, line 13, delete "standalone" and insert --stand-alone--;
In Column 2, line 17, after "either" insert --in--;
In Column 3, line 26, delete "10";
In Column 5, line 4, delete "10";
In Column 7, line 45, delete "a" and insert --an--;
In Column 7, line 60, delete "15";
In Column 8, line 1, delete "sized" and insert --sizes--;
In Column 9, line 36, delete "15";
In Column 9, line 60, insert space before "output";
In Column 10, line 17, delete "THe" and insert --The--;
In Column 10, line 34, delete "(";
In Column 10, line 46, after "alternatively" insert --be--;
In Column 10, line 50, delete "THese" and insert --These--;
In Column 11, line 4, start a new paragraph at the word "Despite".
```

Signed and Sealed this

Eleventh Day of October, 1994

Attest:

BRUCE LEHMAN

Attesting Officer

Commissioner of Patents and Trademarks